(12) United States Patent
Yu et al.

(10) Patent No.: US 10,519,417 B2
(45) Date of Patent: Dec. 31, 2019

(54) HIGH-SECRETION HEAT-RESISTANT YEAST GENETICALLY ENGINEERED STRAIN AND APPLICATION THEREOF

(71) Applicant: Jiangnan University, Wuxi (CN)

(72) Inventors: Xiaowei Yu, Wuxi (CN); Yan Xu, Wuxi (CN)

(73) Assignee: Jiangnan University, Wuxi, Jiangsu (CN)

( * ) Notice: Subject to any disclaimer, the term of this patent is extended or adjusted under 35 U.S.C. 154(b) by 0 days.

(21) Appl. No.: 15/746,621

(22) PCT Filed: Jul. 1, 2016

(86) PCT No.: PCT/CN2016/088057
§ 371 (c)(1),
(2) Date: Apr. 30, 2018

(87) PCT Pub. No.: WO2017/201815
PCT Pub. Date: Nov. 30, 2017

(65) Prior Publication Data
US 2019/0071632 A1    Mar. 7, 2019

(30) Foreign Application Priority Data

May 26, 2016 (CN) .......................... 2016 1 0356374

(51) Int. Cl.
| | |
|---|---|
| *C12N 1/16* | (2006.01) |
| *C12N 15/81* | (2006.01) |
| *C12N 9/18* | (2006.01) |
| *C12N 9/50* | (2006.01) |

(52) U.S. Cl.
CPC .................. *C12N 1/16* (2013.01); *C12N 9/18* (2013.01); *C12N 9/50* (2013.01); *C12Y 301/01003* (2013.01); *C12Y 301/01004* (2013.01)

(58) Field of Classification Search
None
See application file for complete search history.

(56) References Cited

U.S. PATENT DOCUMENTS

2005/0108789 A1* 5/2005 Gramatikova ........... C12N 9/16
800/281

FOREIGN PATENT DOCUMENTS

| CN | 104164375 A | 11/2014 |
|---|---|---|
| TW | 201612310 A | 4/2016 |

OTHER PUBLICATIONS

Ahmad et al. Protein expression in Pichia pastoris: recent achievements and perspectives for heterologous protein production. Published online Apr. 18, 2014. Appl. Microbiol. Biotechnol. vol. 98, 5301-5317. (Year: 2014).*

* cited by examiner

*Primary Examiner* — Channing S Mahatan
(74) *Attorney, Agent, or Firm* — IPro, PLLC; Na Xu (57) ABSTRACT

The invention discloses a high-secretion heat-resistant yeast genetically engineered strain and application thereof, belonging to the field of biotechnology. Mutagenesis and domestication are performed to obtain the yeast genetically engineered strain capable of expressing a lipase gene at a high secretion level at high temperature. The strain is collected by China Center for Type Culture Collection (CCTCC), and the collection number is CCTCC NO: M 2016278. The sequencing analysis shows that the lipase gene and promoter sequence thereof are not mutated, which indicates that the high-secretion expression of the lipase gene by the mutant strain is caused by mutation of other gene sequences in the genome. By knocking out the lipase gene in homologous double-crossover way, the constructed knockout strain can be used as an expression host of other exogenous proteins, can be used for enhancing the expression level of other exogenous genes, and can be subjected to fermentation under high-temperature fermentation conditions.

8 Claims, 3 Drawing Sheets

Specification includes a Sequence Listing.

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic DNA

<400> SEQUENCE: 1
gactggttcc aattgacaag c                                     21

<210> SEQ ID NO 2
<211> LENGTH: 22
<212> TYPE: DNA
<213> ORGANISM: Artificial Sequence
<220> FEATURE:
<223> OTHER INFORMATION: Synthetic DNA

<400> SEQUENCE: 2
cttacaaaca gcttccttcg tt                                    22
```

HIGH-SECRETION HEAT-RESISTANT YEAST GENETICALLY ENGINEERED STRAIN AND APPLICATION THEREOF

TECHNICAL FIELD

The disclosure herein relates to the field of biotechnology, which relates to a high-secretion heat-resistant yeast genetically engineered strain and application thereof

BACKGROUND

Yeasts are important producing strains in alcohol and food industries. As the energy crisis and environmental awareness of the human being are increasingly enhanced, the use of fuel alcohol instead of gasoline is becoming a development trend. Heat-resistant yeasts can reduce the trouble and cost caused by cooling in alcohol production, thereby ensuring the normal proceeding of industrial fermentation at high temperature; and therefore, screening about heat-resistant yeasts becomes a hot spot of research. In recent years, many artificially bred heat-resistant yeast strains have been put into production, and have gained good economic benefits.

As early as the middle of the 20th century, Chinese microbiologists started to work on domesticated breeding and research on heat-resistant yeasts capable of being fermented by using molasses as a raw material. Currently, many artificially bred heat-resistant yeast strains have been put into production, and have gained good economic benefits. It is reported that the strains for production are domesticated and screened to obtain the heat-resistant alcohol yeast applicable to corn mash fermentation. For quite a long time, breeding of heat-resistant strains mainly depends on screening from nature and high-temperature domestication. The researchers enhance the maximum growth temperature of *Saccharomyces cerevisiae* by 3° C. through chemical mutagenesis and genetic recombination; by combining high-temperature domestication/ultraviolet mutagenesis and thermal shock, the fermentation temperature of the alcohol-producing yeast is increased by 6° C.; a protoplast fusion technique is utilized, so that the alcohol yield of *Saccharomyces cerevisiae* and respiratory-deficient heat-resistant *Kluyveromyces* under the condition of 45° C. can reach 7.4%; by means of high-temperature domestication, the *Saccharomyces cerevisiae* can grow at 40° C.; by using screening from nature and ultraviolet mutagenesis, the alcohol yield of the *Saccharomyces cerevisiae* under the condition of 42° C. is increased; and a normal-pressure room-temperature plasma mutagenesis technique is utilized to obtain a high-yield oleaginous yeast.

*Pichia pastoris* (*P. pastoris* for short) is a widely used eukaryon expression system, which has the obvious advantages of high exogenous protein expression level, simple nutrients, easy induction and the like, but has the defect of high energy consumption caused by low induction temperature and has the problem that the expression of exogenous proteins is obviously inhibited when the fermentation is performed under high-temperature conditions. Up to now, there is no research report that the fermentation of *P. pastoris* at high temperature does not influence the expression of exogenous proteins.

The optimal temperature for growth of *P. pastoris* is 28-30° C.; besides, previous research has shown that the reduction of induction temperature can promote the expression of exogenous proteins; and under low-temperature conditions, the activity and transcription level of alcohol oxidase AOX can be enhanced, and the apoptosis of the strain is lowered. [Sue Macauley-Patrick, Mariana L. Fazenda, Brian McNeil and Linda M. Harvey, Heterologous protein production using the *Pichia pastoris* expression system. Yeast 2005, 22: 249-270; Min Zhaosheng, Guo Huiming, Yan Xu, Hong Housheng. *P. pastoris* High-density Fermentation Research Progress, Biotechnology Bulletin, 2014, 3:42-49]. The research of Li, et al [Li Z, Xiong F, Lin Q, et al. 2001. Low temperature increases the yield of biologically active herring antifreeze protein in *Pichia pastoris*. Protein Expression Purification, 21(3): 438-445.] finds that after the induction temperature is lowered from 30° C. to 23° C., the expression level of the herring antifreeze protein is increased from 5.3 mg/L to 18.0 mg/L, and the cell activity is obviously enhanced. The preliminary research of the research group compares the effects of different induction temperatures in a 7 L fermentation tank on the expression level of *Rhizopus chinensis* leader peptide lipase in *P. pastoris*. The experiments indicate that under the condition of 28° C., the maximum enzyme activity can reach 1412.5 U/mL, which is as 2.3 times as that under the condition of 30° C. and as 1.3 times as that under the condition of 25° C.; it is detected that as the induction temperature becomes lower, the death rate of the strain gets lower; however, under the condition of 25° C., the growth rate of the strain is lower, and the expression of enzyme activity is affected [Wang Tongchun, Yu Xiaowei, Xu Yan, Research of Regulation of Expression and Stability of *Rhizopus chinensis* Leader Peptide Lipase by Induction Temperature, *Industrial Microbiology*, 2010, 4:34-39]. All the existing research reports show that the induction temperature for expressing exogenous proteins by using *P. pastoris* is controlled at 30° C. or below so as to obtain a higher exogenous protein expression level. However, the lower induction temperature requires abundant energy consumption for lowering the temperature in industrial production; and therefore, it is urgent to develop a *Pichia pastoris* expression strain capable of efficiently inducing the expression of exogenous proteins under high-temperature conditions.

SUMMARY

In order to solve the problems above, a heat-resistant *Pichia pastoris* strain capable of efficiently expressing exogenous proteins is obtained by screening in the invention; and in the invention, the application performance of *Pichia pastoris* is enhanced, and the heat resistance mechanism is analyzed. The heat-resistant *Pichia pastoris* strain in the invention can perform fermentation at higher temperature, thereby bringing the following advantages: 1. lowering the expenses on cooling in fermentation, and lowering the production cost; and 2. lowering the pollution (the enhanced fermentation temperature inhibits the pollution of many infectious microbes).

The invention firstly aims to provide a high-secretion heat-resistant *Pichia pastoris*, which has been collected by China Center for Type Culture Collection (CCTCC) on May 24, 2016; the collection address is Wuhan University, Wuhan, PRC; and the collection number is CCTCC NO: M 2016278.

The invention secondly aims to provide an application method of the *Pichia pastoris* CCTCC NO: M 2016278, which is used for producing proteins or other biological products (such as production of alcohol and some other metabolites after modification of metabolism).

In an implementation of the invention, the production is performed at 40° C. or below.

In an implementation of the invention, the application method is to produce lipase by using fermentation of the *Pichia pastoris* CCTCC NO: M 2016278; and the method is to produce lipase by inducing fermentation of the *Pichia pastoris* at 40° C. or below.

The application comprises: knocking out the lipase gene in the *Pichia pastoris* CCTCC NO: M 2016278 to obtain the knockout strain, then constructing a recombinant strain expressing exogenous protein gene by using the knockout strain as a host, and producing proteins by using the recombinant strain.

In an implementation of the invention, the 40° C. or below refers to 28° C.–40° C.

In an implementation of the invention, the application method comprises: inoculating a *Pichia pastoris* seed solution in a glycerol growth phase culture medium, and performing a glycerol intermittent supplement stage after the substrate glycerol in the culture medium is basically exhausted; when the induced strain concentration (dry cell weight g/L) is 36 g/L, stopping supplementing the glycerol, keeping such state until the glycerol is completely exhausted, and then feeding a methanol induction solution; slowly increasing the methanol supplementing rate at the beginning, increasing the feeding rate to keep the methanol concentration at 0.1±0.02% (V/V) or so after the strain gradually adapts to methanol, gradually enhancing the induction temperature from 35° C. to 40° C. within 5 h, and keeping the value of dissolved oxygen at 10%-20%, thereby inducing the expression of the lipase.

In an implementation of the invention, the application method comprises: knocking out the lipase gene in the *Pichia pastoris* CCTCC NO: M 2016278 to obtain the knockout strain, then constructing a recombinant strain expressing exogenous protein gene by using the knockout strain as a host, and performing production by using the recombinant strain.

In an implementation of the invention, the knockout refers to knockout by homologous double-crossover.

In an implementation of the invention, the exogenous gene is a phospholipase gene, a *Rhizopus oryzae* lipase gene or a proline protease gene.

The invention thirdly aims to provide a strain obtained by performing any modification on the basis of the *Pichia pastoris* CCTCC NO: M 2016278.

In an implementation of the invention, the modification refers to mutagenesis, domestication or genetic modification on the *Pichia pastoris* CCTCC NO: M 2016278.

In an implementation of the invention, the genetic modification refers to knockout of a lipase gene in the *Pichia pastoris* CCTCC NO: M 2016278 by homologous double-crossover.

In an implementation of the invention, the genetic modification comprises: knocking out the lipase gene in the *Pichia pastoris* CCTCC NO: M 2016278 to obtain the knockout strain, and then using the knockout strain as a host for expressing the exogenous gene.

In an implementation of the invention, the exogenous gene is a phospholipase gene, a *Rhizopus oryzae* lipase gene or a proline protease gene.

The invention fourthly aims to provide application of the modified strain, which is used for producing enzymes or other biological products (such as production of alcohol and some other metabolites after modification of metabolism) by fermentation.

The invention has the following advantages:

(1) The high-secretion heat-resistant *Pichia pastoris* in the invention has high trehalose content, can resist a 50° C. water bath for 45 min, and can produce enzymes by induced culture at 40° C. or below.

(2) When the high-secretion heat-resistant *Pichia pastoris* in the invention is used for producing lipase by fermentation, the extracellular lipase activity reaches 17750 U/mL after fermentation for 84 h, and the extracellular protein concentration reaches 11.7 g/L after 78 h.

(3) The lipase gene and promoter sequence thereof in the strain of the invention are not mutated, which indicates that the high-secretion heat-resistant *Pichia pastoris* can express the lipase gene at high secretion level because of mutation of other gene sequences in the genome. The invention provides a *Pichia pastoris* host strain, which is obtained by knocking out the lipase gene in the CCTCC NO: M 2016278 in a homologous double-crossover mode and thus is used for enhancing the expression level of other exogenous genes. When the knockout strain is used as the host strain to express a phospholipase gene, a *Rhizopus oryzae* lipase gene and a proline protease gene, the enzyme activity levels under the culture condition of 40° C. can be respectively enhanced by 3 times, 9.1 times and 2.5 times.

Biological Material Collection:

A high-secretion heat-resistant *Pichia pastoris* strain, of which the taxonomic name is *Pichia pastoris*, was collected by China Center for Type Culture Collection (CCTCC) on May 24, 2016; the collection address is Wuhan University, Wuhan, PRC; and the collection number is CCTCC NO: M 2016278.

BRIEF DESCRIPTION OF FIGURES

FIG. 5: Schematic diagram of principles of a target gene (lipase gene) in homologous double-crossover knockout *Pichia pastoris* genome, wherein, HIS4 represents a wild type histidine dehydrogenase gene; his4 and his4* represent different mutation types of histidine dehydrogenase genes; His⁻ represents a histidine auxotroph; His represents a non-histidine auxotroph; 5'AOX1 (5'P$_{AOX1}$) represents a promoter of an ethanol oxidase gene AOX1; 3'AOX1 represents a 3' flanking sequence of an ethanol oxidase gene AOX1; TT represents an ethanol oxidase gene AOX1 terminator; A and B represent homologous recombinant two side arm sequences; ZeoR represents a Zeocin resistance gene sequence; Kan represents a G418 resistance gene sequence; and Gene of interest represents an exogenous gene sequence, and is a lipase gene sequence proRCL in the application.

DETAILED DESCRIPTION

Reagents and Strain

Original strain: a *Pichia pastoris* genetically engineered strain expressing a lipase gene [Yu, X. W., L. L. Wang, and Y. Xu (2009) *Rhizopus chinensis* lipase: Gene cloning, expression in *Pichia pastoris* and properties. J. Mol. Catal. B-Enzym. 57: 304-311; Dan Wu, Xiao-Wei Yu, Tong Chun Wang, Rui Wang, and Yan Xu. High Yield *Rhizopus* chinenisis prolipase Production in *Pichia pastoris*: Impact of Methanol Concentration. *Biotechnology and Bioprocess Engineering*, 2011, 16: 305-311].

YPD liquid medium: yeast extract 10 g/L, peptone 20 g/L, glucose 20 g/L.

Screening medium: yeast extract 10 g/L, peptone 20 g/L, glucose 20 g/L, agar 2%, G418 0.25 g/L, rhodamine B $1 \times 10^{-3}$%, 1% olive oil PVA emulsion.

YPD-G418 solid medium: yeast extract 10 g/L, peptone 20 g/L, glucose 20 g/L, agar 2%, G418 0.25 g/L.

YPD-Zeo solid medium: yeast extract 10 g/L, peptone 20 g/L, glucose 20 g/L, agar 2%, Zeocin 100 µg/ml.

MD solid medium: glucose 20 g/L, YNB 1.34%, biotin $4 \times 10^{-5}$%, agar powder 2%.

MD-G418 solid medium: glucose 20 g/L, YNB 1.34%, biotin $4 \times 10^{-5}$%, agar powder 2%, G418 0.25 g/L.

BMGY medium: yeast extract 10 g/L, peptone 20 g/L, glycerol 10 g/L, phosphate buffer 100 mmol/L, pH 6.0, YNB 1.34%, biotin $4 \times 10^{-5}$%.

BMMY medium: yeast extract 10 g/L, peptone 20 g/L, methanol 0.5 g/L, phosphate buffer 100 mmol/L, pH 6.0, YNB 1.34%, biotin $4 \times 10^{-5}$%.

Sodium acetate sporulation medium: anhydrous sodium acetate 8.2 g/L, potassium chloride 1.8 g/L, glucose 1 g/L, yeast extract 2.5 g/L, agar powder 2%.

Glycerol growth phase medium (basal salt medium): $CaSO_4$ 0.93 g/L, 85% $H_3PO_4$ 28.70 mL/L, $MgSO_4.7H_2O$ 14.90 g/L, $K_2SO_4$ 18.20 g/L, KOH 4.13 g/L. The medium is made into a fermentation medium containing 4% (W/V) glycerol and 4 mL/L $PTM_1$.

Glycerol transition phase fed-batch medium: 50% (W/V) glycerol, wherein the $PTM_1$ content is 12 mL/L.

Methanol induced phase culture solution: pure methanol induction solution, wherein the $PTM_1$ content is 24 mL/L.

Microelement $PTM_1$ solution: $CuSO_4.5H_2O$ 6.0 g/L, KI 0.08 g/L, $MnSO_4.H_2O$ 3.0 g/L, $Na_2MoO_4.2H_2O$ 0.2 g/L, $H_3BO_3$ 0.02 g/L, $ZnSO_4.7H_2O$ 42.2 g/L, $FeSO_4.7H_2O$ 65.0 g/L, $CoCl_2.6H_2O$ 0.5 g/L, Biotin 0.2 g/L, $H_2SO_4$ 5.0 mL/L.

Embodiment 1: Strain Mutagenesis Methods

Ultraviolet mutagenesis, chemical reagent mutagenesis, normal-pressure room-temperature plasma mutagenesis and other mutagenesis methods are adopted.

Reference for ultraviolet, diethyl sulfate and nitrosoguanidine mutagenesis methods [Mutagenic Effects of Different Mutagenesis Methods on Hyaluronic Acid-producing Strain Sz560, Ding Yong, Shi Xiaoyong, Zhang Xinming, *Food Research and Development*, 2012, 12:50-53]. Reference for the normal-pressure room-temperature plasma mutagenesis method [Mutation Breeding of *Saccharomyces cerevisiae* with Low Purine by Atmospheric and Room Temperature Plasma, Kang Fushuai, Yan Bing, Lv Nanquan, Zhou Shishui, *Modern Food Science and Technology*, 2014, 2:188-191]. In the research process, the methods above and different combinations of the methods above are utilized to perform mutagenesis on the strain.

Embodiment 2: Strain Domestication

High-temperature domestication is performed on the strain mixture (mixed strains) obtained by different mutagenesis methods. The mixed strains are inoculated into a fresh YPD medium and subjected to 32° C., 34° C., 36° C., 38° C. and 40° C. temperature gradient increase domestication culture. The mixed strains are inoculated into 100 mL of fresh YPD medium and cultured at 32° C., and meanwhile, the original strain is inoculated into 100 mL of fresh YPD medium and cultured at 30° C., wherein the inoculum size is an original OD of 0.1. 72 h of culture is primary domestication. After the primary domestication is finished, the OD is measured, if the ratio of the OD value under high-temperature conditions to the OD value of the original strain under 30° C. conditions is greater than 1, the next temperature gradient domestication is performed, and if not, the mixed strains are inoculated into a fresh medium and subjected secondary domestication at such temperature until the ratio is greater than 1. Finally, in order to complete the domestication, 1 cycle is performed at 32° C., 3 cycles are performed at 34° C., 10 cycles are performed at 36° C., 28 cycles are performed at 38° C., and 45 cycles are performed at 40° C.

Embodiment 3: Monoclonal Separation of Temperature-Resistant High-Secretion Domesticated Strain 1) Uniformly coating the mutated and domesticated strain on the screening medium, and culturing in a 40° C. incubator for 3 days.

2) Picking 28 monoclones with the biggest colonies and most obvious red transparent rings, and performing overnight culture in 5 mL of fresh YPD medium. A bigger colony represents a higher activity at high temperature, and a more obvious red transparent ring represents a higher activity of the secretory-expressed lipase.

3) Respectively inoculating 28 monoclones into 100 mL of fresh YPD medium, performing 40° C. 200 rpm constant-temperature culture for 3 days, and screening to obtain 5 strains with the best growth conditions for the follow-up experiments, wherein the 5 strains are respectively named 6, D, N, J and H.

Embodiment 4: Preparation of Temperature-Resistant Monoclone Haploid

In order to enhance the genetic stability of the strain, a high-temperature-resistant monoclone haploid strain is prepared in the embodiment.

1) Culturing for 72 h by using the YPD-G418 liquid medium at 40° C., after 2 passages, coating the strain on the sodium acetate sporulation medium, culturing at 25° C. for 3-7 days, sampling, and performing microscopic examination.

2) Microscopic examination and staining: staining by using 5% malachite green and a 0.5% safranine staining solution.

The method comprises: preparing a strain suspension, adding 1-2 drops into a small test tube in a water bath, picking 2-3 loops of lawns by using an inoculating loop, putting the lawns into the test tube, and stirring uniformly, thereby preparing a thick strain suspension.

Staining of malachite green staining solution: adding 2-3 drops of the malachite green staining solution into the test tube, uniformly mixing the malachite green staining solution with the strain suspension, putting the test tube into a beaker in a water bath, and heating to perform staining for 20 min.

Fixation of smear: taking several loops of the strain suspension on the bottom of the test tube by using the inoculating loop, putting the strain suspension on a clean slide, coating into a film, and passing the smear through flame 3 times to perform warm fixation.

De-staining: flushing with water until the effluent liquid is not green.

Re-staining: staining for 1-2 min by using a safranine staining solution, pouring out the staining solution, washing with water, and suck drying with filter paper.

Microscopic examination: after drying, observing with an oil immersion lens, wherein ascospores are green, and trophocytes are red.

3) Ascospore release method by treating with helicase: taking a right amount of yeast in which ascospores are formed from the sporulation medium, preparing an ascospore suspension by using 0.9% normal saline, taking 200 μL of the suspension, centrifugating, discarding the supernate, adding 200 μL of 3% helicase solution, and performing enzymolysis in a 30° C. water bath for 2 h.

4) Separation of haploid: respectively treating the helicase-treated ascospore haploid and diploid mixed strain suspension in a 58° C. water bath for 12 min, adding quartz sand, oscillating at 30° C. for 30 min to scatter the ascospores, quickly diluting by $10^{-2}$-$10^{-3}$, coating on the YPD+G418 medium, and culturing at 35° C. for 2 days to 3 days. The grown clone is the haploid clone.

Embodiment 5: Temperature-Resistance Phenotype Detection of Mutant Strains

Picking the original strain and 5 temperature-resistant strains from the plate, putting into 5 mL of YPD medium, performing overnight culture, collecting the strains, washing the strains with normal saline twice, and suspending the strains so that the OD of the strain suspension is 1. After treating in a 50° C. sublethal-temperature water bath for 45 min, quickly cooling, performing 1, $10^{-1}$, $10^{-2}$, $10^{-3}$ and $10^{-4}$ gradient dilution, absorbing 4 μL, dripping onto the YPD-G-418 solid medium, and culturing in a 30° C. constant-temperature incubator for 3 days.

Figure 1:
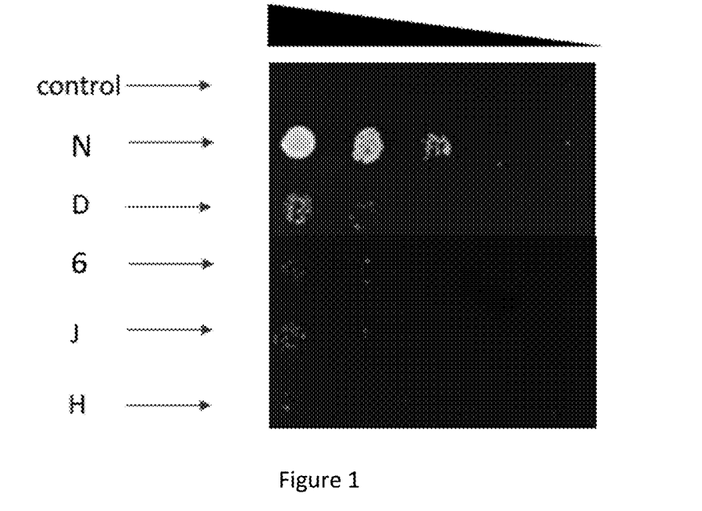
FIG. 1: Temperature-resistance phenotype detection plate growth view of a mutant strain.

The result shows (FIG. 1) that the original strains in the control group are 100% killed, and the No. N strain (the *Pichia pastoris* CCTCC NO: M 2016278 in the invention) is most temperature-resistant.

Embodiment 6: Determination of Intracellular Trehalose Contents in Mutant Strains The existing reports show that a high-temperature-resistant strain generally has a higher intracellular trehalose content; the trehalose can be used as a protective substance for yeast cells; and in an extreme environment, organisms can resist injuries from the outside by regulating the synthesis of trehalose, so the trehalose content is considered as an important index of resistance of yeast.

1) Making of Standard Curve

Taking 6 dry test tubes, sequentially adding 0, 0.1, 0.2, 0.3, 0.4 and 0.5 mL of 0.1 mg/mL standard trehalose solution, sequentially adding distilled water to 1 mL, adding 4 mL of anthracenone reagent (dissolving 0.2 g of anthracenone in 100 mL of 80% sulfuric acid) into each tube, and shaking uniformly. Accurately boiling in a boiling water bath for 10 min, standing at room temperature for 10 min, performing zero adjustment by using the No. 1 test tube solution, and performing colorimetric determination A620 (performing determination on the sample at the same time). By using the standard trehalose solution concentration as the horizontal ordinates and the absorbance as the vertical coordinates, making the standard curve, wherein A620=9.62C-0.0033, $R^2$=0.99, and C represents the trehalose concentration (mg/mL).

2) Extraction of Intracellular Trehalose

Adding 20 mL of the strain suspension, which has been cultured to the $OD_{600}$ of 6, into a 50 mL centrifuge tube, centrifugating at 4000 rpm for 5 min, removing the supernate, performing centrifuge washing on the strain by using frozen distilled water under the condition of 4000 rpm for 5 min three times, adding 4 mL of 0.5 mol/L trichloroacetic acid (TCA), uniformly mixing, then standing in an ice bath for 20 min (oscillating and mixing uniformly every 5 minutes in the period), centrifugating the mixed solution at 4000 rpm for 5 min, collecting the supernate, and diluting with water by 10 times to totally obtain 40 mL of extracting solution.

3) Determination of Trehalose Content

Adding 1 mL of extracting solution into a trehalose burette containing 4 mL of anthracenone, boiling in boiling water for 10 min, cooling with running water, then standing at room temperature for 10 min, reading the absorbance under the condition of 620 nm, and finally, obtaining the trehalose concentration according to the standard curve.

Figure 2:
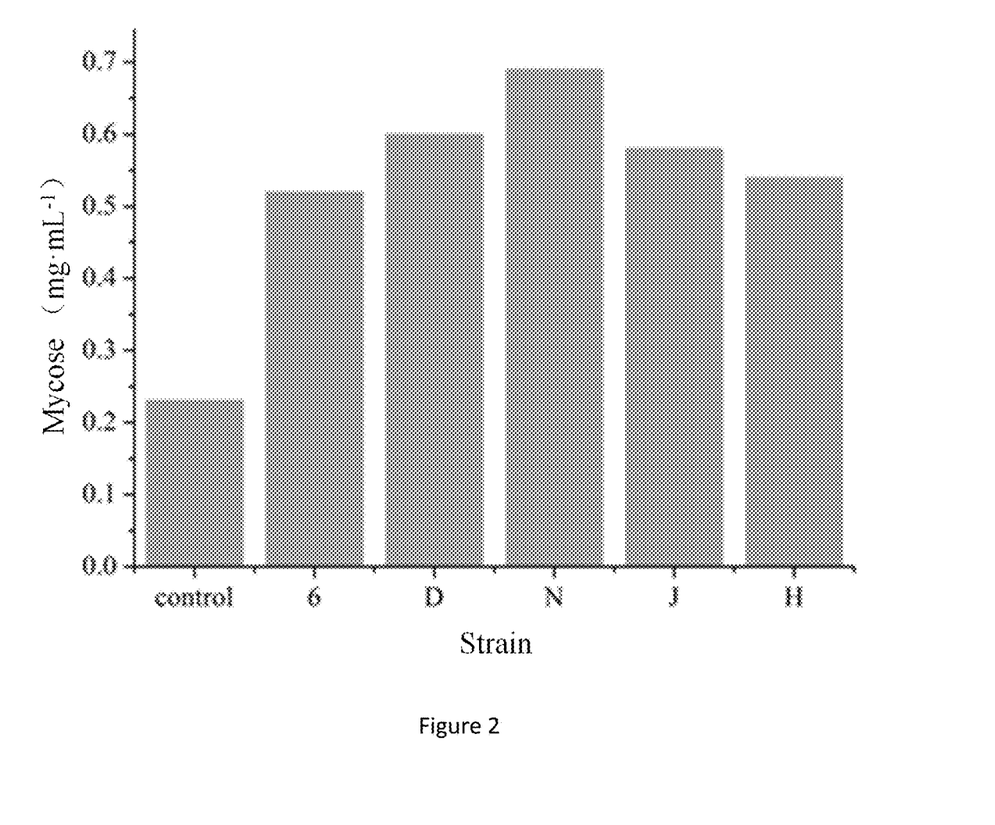
FIG. 2: Determination of yeast intracellular trehalose content.

4) The result is as shown in FIG. 2. Compared with the original strain in the control, the intracellular trehalose contents of the mutant strains 6, D, N, J and H are respectively obviously higher than that of the original strain, wherein the No. N mutant strain (the *Pichia pastoris* CCTCC NO: M 2016278 in the invention) has the highest trehalose content.

Embodiment 7: Passage Stability Detection and Shake-Flask Fermentation Culture of Mutant Strains Streaking the No. N mutant strain on the YPD solid medium, culturing at 40° C. for 3 days, picking the single colony, streaking, inoculating into a new YPD solid medium, culturing at 40° C. for 3 days, performing continuous passage like this for totally 20 times, and then performing shake-flask fermentation culture.

The shake-flask fermentation culture method comprises:

1) respectively inoculating the No. N mutant strain and the original strain into 25 mL of BMGY medium, and culturing at 40° C. under the condition of 200 rpm over night.

2) collecting the strain, centrifugating, removing the supernate, resuspending, then inoculating into 100 mL of BMMY medium, and while keeping the initial $OD_{600}$ of different strains the same, performing fermentation culture in a 40° C. constant-temperature shaking table under the condition of 200 rpm.

3) adding 1 mL of methanol every 24 h to induce the expression of lipase, and sampling for measuring the strain concentration, extracellular protein concentration and extracellular lipase activity.

The result shows that after 20 continuous passages, the variation range of the lipase activity in the shake-flask fermentation supernate is within 5%, which indicates favorable genetic stability of the mutant strain.

Besides 40° C., the temperature conditions of 28° C., 30° C., 35° C. and 38° C. are also selected as the temperatures of shake-flask fermentation culture to perform expression detection. The results show that under the conditions of 28° C., 30° C., 35° C., 38° C. and 40° C., the lipase activities of the No. N mutant strain in the shake-flask fermentation supernate are respectively 756 U/mL, 750 U/mL, 645 U/mL, 638 U/mL and 620 U/mL, and the lipase activities of the original strain are respectively 120 U/mL, 50 U/mL, 0 U/mL, 0 U/mL and 0 U/mL, which indicates that the mutant strain can efficiently express lipase under the induction temperature condition of 40° C. or below.

Embodiment 8: 3 L Fermentation Tank Bench-Scale Testing of Mutant Strains (1) Plate Seed Culture Streaking on a YPD plate, and culturing at 30° C. for 3 days or so.

(2) Shake-Flask Culture

Picking a colony with good growth form in a super-clean bench, inoculating into a 250 mL triangular flask, culturing for about 22 h, sampling, and finishing the culture when the absorbance is detected to be 2-6, wherein the loading volume is 50 mL.

(3) Fermentation Tank Culture

Accurately preparing 1 L of glycerol growth phase medium in a 3 L fermentation tank, installing a baffle, stirring paddles, a supplement needle and the like, inserting a defoaming electrode of which the DO and pH are calibrated off line, sealing to protect an electrode tip, connecting two air filters while tying up with clips in the middle, connecting a sampler, and sterilizing in a sterilizer at 121° C. for 20 min. Taking out, cooling at room temperature, connecting a fermentation regulator, regulating the air flow to 2.5 L/min, the initial stirring speed to 300 r/min and the strain growth temperature to 35° C., and automatically regulating the pH value to 5.5 by using ammonia water. Merging seed solutions in 5 flasks, adding 10.875 mL of $PTM_1$ solution subjected to filtration sterilization, and performing flame inoculation (the inoculum size is 10%); and after the DO value becomes stable (100%), performing coil cooling or heating-jacket heating and automatic feeding of ammonia water to control the temperature and pH at the set value in the glycerol growth phase period, and regulating the speed to keep the value of dissolved oxygen at 50% or above. Fermenting for 20-25 h, wherein the value of dissolved oxygen sharply increases at this time, which indicates that the substrate glycerol in the medium is basically exhausted; and keeping such state for half an hour, starting feeding 50% of the glycerol transition phase medium, and entering the glycerol intermittent supplement stage. Meanwhile, connecting a methanol controller, and preheating.

Taking a sample for detecting the strain concentration every 4 h, stopping supplementing the glycerol when the value reaches the induced strain concentration (dry cell weight g/L) of 36 g/L, keeping such state for 30 min until the glycerol is completely exhausted (in order to prevent the surplus glycerol from repressing the promoter AOX1), regulating the value of dissolved oxygen to 100% again, and starting entering the methanol phase. Feeding a methanol induction solution into the fermentation liquid at variable speed by using a methanol controller, wherein the methanol supplement speed is slowly increased at the beginning to avoid the situation that the strain is poisoned due to incapability of adapting to methanol (the adaptation period is 8 h or so), the feeding speed is increased to keep the methanol concentration at 0.1±0.02% (V/V) or so after the strain gradually adapts to the methanol, and meanwhile, the induction temperature is gradually enhanced from 35° C. to 40° C. within 5 h so as to gradually enhance the adaptability of the strain to methanol. Keeping the value of dissolved oxygen at 10%-20% by regulating the speed, increasing the flow rate and adopting the pure oxygen introduction way, thereby inducing the efficient expression of lipase.

Figure 3:
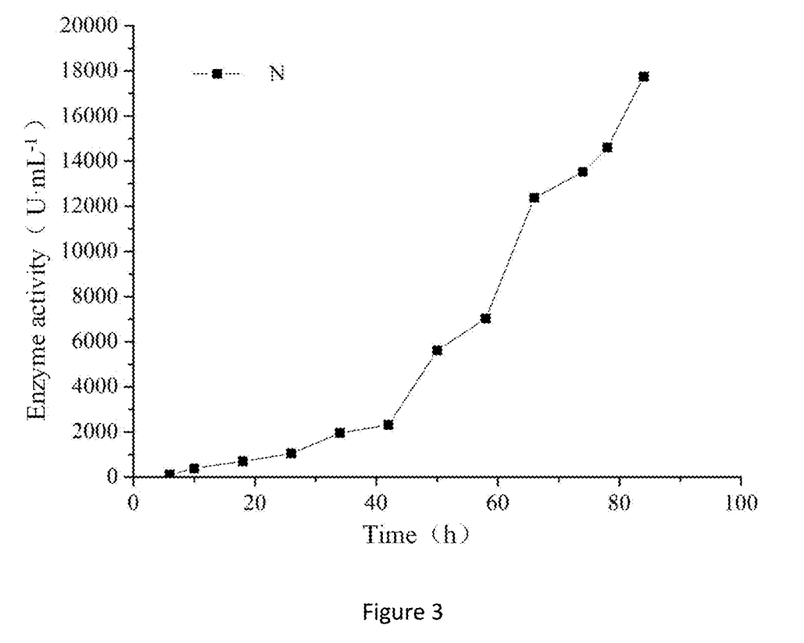
FIG. 3: Time-history curve of activity of lipase in No. N fermentation supernate of the mutant strain.
Figure 4:
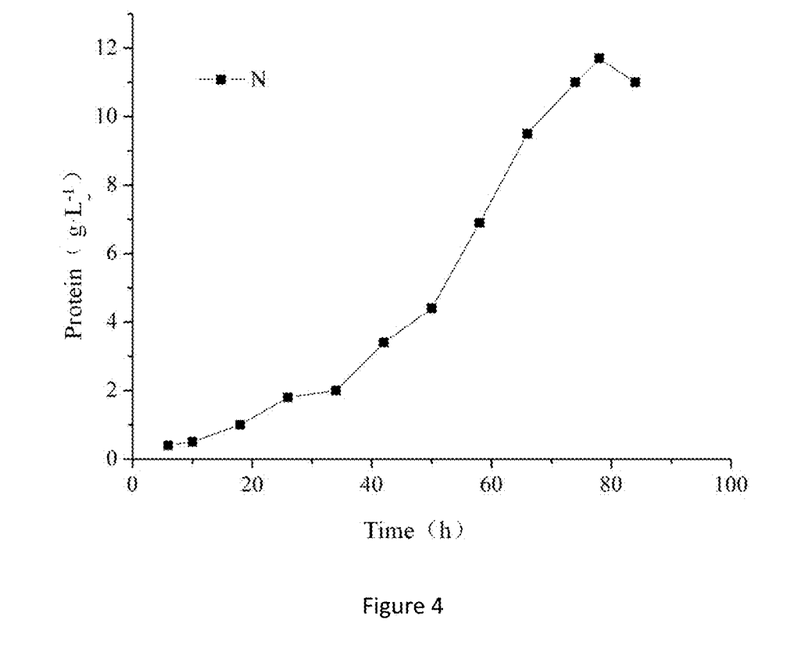
FIG. 4: Time-history curve of concentration of protein in No. N fermentation supernate of the mutant strain.

(4) The fermentation result is as follows: as shown in FIG. 3 and FIG. 4, by taking the No. N strain as an example, the extracellular lipase activity continuously increases to 17750 U/mL as the induction time increases to 84 h, and the extracellular protein concentration reaches the maximum 11.7 g/L after 78 h.

It is reported in the literature that under the condition of 28° C., the maximum enzyme activity of the original strain can reach 1412.5 U/mL, which is as 2.3 times as that under the condition of 30° C. [Research of Regulation of Expression and Stability of *Rhizopus chinensis* Leader Peptide Lipase by Induction Temperature, Wang Tongchun, Yu Xiaowei, Xu Yan, Industrial Microbiology, 2010, 4:34-39]; and after the methanol induction concentration is optimized (consistent with the methanol induction concentration adopted by the invention), the maximum activity of lipase expressed by the original strain is only 2,130 U/mL [Dan Wu, Xiao-Wei Yu, Tong Chun Wang, Rui Wang, and Yan Xu. High Yield *Rhizopus* chinenisis prolipase Production in *Pichia pastoris*: Impact of Methanol Concentration. *Biotechnology and Bioprocess Engineering*, 2011, 16: 305-311], and the lipase activity in the invention is as 8.3 times as that of the original strain. Besides, under high-temperature fermentation conditions of the invention, the original strain basically can not grow normally, and no lipase activity is detected in the supernate.

According to the above analysis, the *Pichia pastoris* genetically engineered strain capable of efficiently secreting and expressing lipase at high temperature is obtained in the invention.

Embodiment 9: Sequencing Identification of Lipase Gene and Promoter Sequence Thereof in Mutant Strain In order to research whether the high-secretion expression of the lipase gene by the mutant strain is caused by the mutation of the lipase gene or promoter gene sequence thereof in the mutagenesis process, the lipase gene and promoter sequence thereof in the mutant strain genome are subjected to PCR amplification and sent to Shanghai Biological Engineering Co., Ltd for sequencing.

Forward primer sequence F: 5'-GACTGGTTCCAATT-GACAAGC-3' (the nucleotide sequence is as shown in SEQ ID NO:1); reverse primer sequence R: 5'-CTTACAAACA-GCTTCCTTCGTT-3' (the nucleotide sequence is as shown in SEQ ID NO:2). The pair of primers can be utilized to amplify the lipase gene and promoter sequence thereof together.

The PCR amplification method comprises:
Step1: 98° C. 30 sec
Step2: 98° C. 10 sec
Step3: 58° C. 45 sec
Step4: 72° C. 90 sec
Step5: go to step2 30 cycles
Step6: 72° C. 10 min
Step7: 10° C. hold The sequencing result shows that the lipase gene and promoter sequence thereof are not mutated, which indicates that the high-secretion expression of the lipase gene by the mutant strain is caused by mutation of other gene sequences in the *Pichia pastoris* genome.

Embodiment 10: Construction of Knockout Strain

Since the No. N mutant strain (*Pichia pastoris* CCTCC NO: M 2016278 in the invention) has the characteristic of high-secretion expression of the lipase gene, it can be deduced that the strain can also be used for enhancing the expression level of other exogenous genes. Thus, a homologous double-crossover method is utilized to knock out the expression cassette comprising the lipase gene from the No. N mutant strain, so as to construct a host strain for expressing other exogenous genes (hereafter referred to as a knockout strain).

Figure 5:
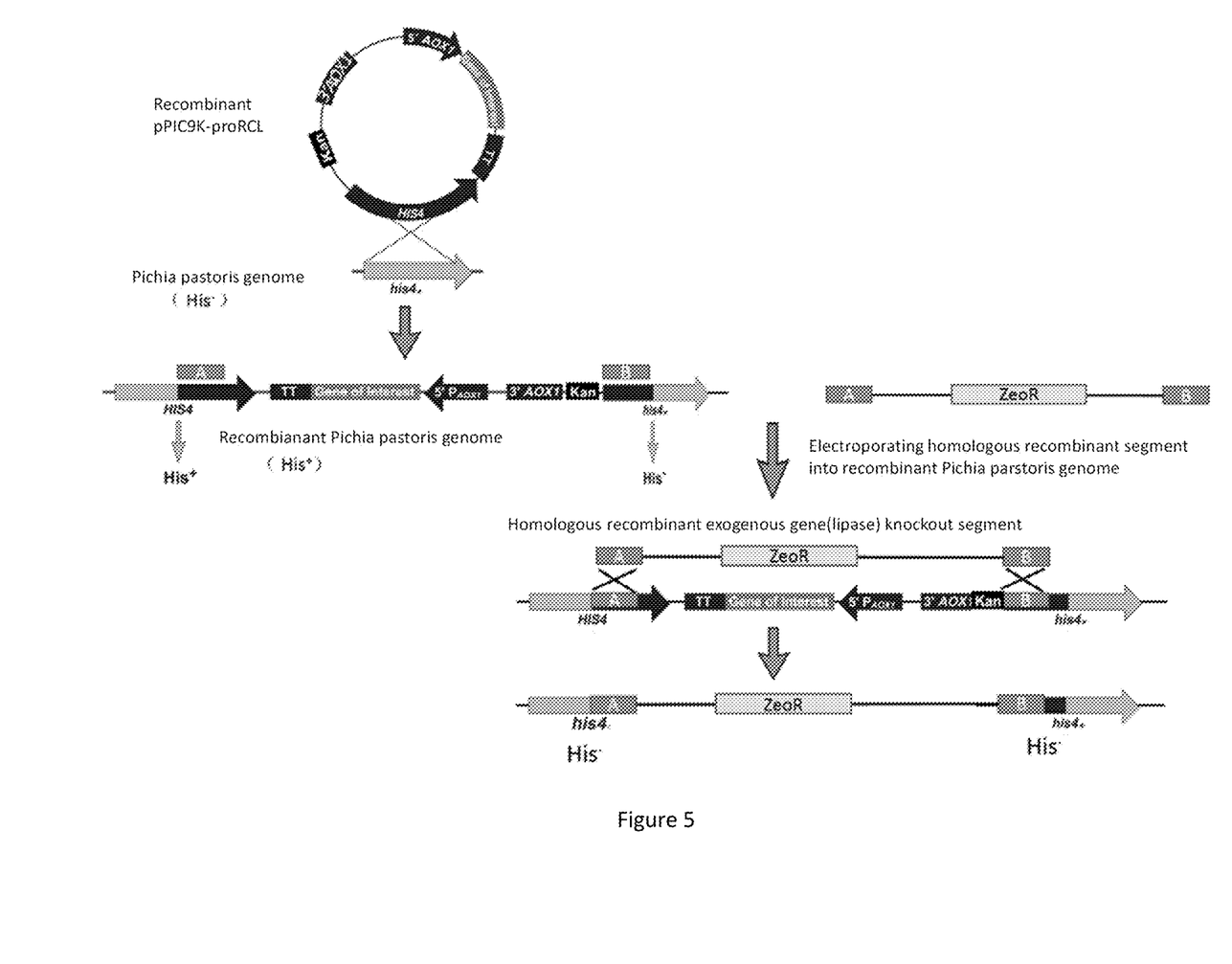

Reference for knockout method (Ni Zhenhua, Zhou Xiangshan, Zhang Yuanxing, Application of Direct Gene Disruption Method in Recombinant *Pichia pastoris, Microbiology China,* 2007, 34:1198-1201.). The knockout principle of the experiment is as shown in FIG. 5. Since only one copy of lipase gene sequence is inserted into the mutant strain, the homologous double-crossover method is utilized to knock out the lipase gene.

Zeocin (bleomycin) resistance screening is utilized to obtain the knockout strain, the strain suspension subjected to electrotransformation is coated on the YPD-Zeo solid medium and cultured at 30° C. for 3 days, and a transformant is selected and subjected to PCR identification. The research proves that the lipase gene is successfully knocked out. *Pichia* Expression Kit (Invitrogen Corporation) is referred to identify whether the knockout strain is of a histidine auxotroph or not, and the identification result is that the knockout strain is of a histidine auxotroph. All this suggests that the knockout strain is successfully constructed.

Embodiment 11: Expression of Phospholipase Gene by Knockout Strain

The knockout strain is used as the host strain to express a phospholipase A2 gene from the reference [Liu A, Yu X W, Sha C, Xu Y. *Streptomyces violaceoruber* Phospholipase A2: Expression in *Pichia pastoris*, Properties, and Application in Oil Degumming. *Applied Biochemistry Biotechnology.* 2015, 175:3195-206.], comprising: after linearizing an expression plasmid pPIC9K-PLA2 reported in the reference by using SalI, electroporating into the knockout strain (The electroporating method comprises: taking a tube of competent cells, transferring into the linearized plasmid which is subjected to enzyme digestion and concentrated, uniformly mixing, transferring into a 2 mm pre-cooled electroporation cuvette, standing on ice for 3-5 min, and performing electroporation, wherein the parameters of the electroporator are set as follows: voltage 1500V, resistance 200Ω, and capacitance 25 μF; after the electroporation, immediately adding 1 mL of 1 mol/L sorbitol solution, uniformly mixing, transferring into a 1.5 mL EP tube, recovering at 30° C. for 1 h, centrifuging, then removing the supernate until 100 μL is left, resuspending the strain, coating on an MD-G418 plate, and culturing in a 30° C. incubator for 3 days to obtain a series of single colony transformants), coating on the MD-G418 plate, and picking monoclones to perform PCR verification, wherein the strain verified to be correct is the successfully constructed *Pichia pastoris* genetically engineered strain expressing phospholipase A2.

Refer to Embodiment 7 for the shake-flask fermentation culture method, comprising: inoculating a positive expression strain into 25 mL of BMGY medium, and culturing at 40° C. under the condition of 200 rpm over night; collecting the strain, centrifuging to remove the supernate, resuspending, then inoculating into 100 mL of BMMY medium, performing fermentation culture in a 40° C. constant-temperature shaking table under the condition of 200 rpm; and performing induced expression by adding 1 mL of methanol every 24 hours, and sampling for measuring the enzyme activity of the phospholipase A2 in the supernate.

The method for measuring the activity of phospholipase A2 comprises:

a. weighing 40.0 g of polyvinyl alcohol (PVA), adding 800 mL of water, heating and stirring in a boiling water bath until all the PVA is dissolved, cooling, and then adding water to reach a constant volume of 1000 mL; filtering through clean double-layer gauze, and taking the filtrate for later use;

b. mixing a phosphate buffer and the PVA in a volume ratio of 19:1 such that the end concentration of PVA is 0.2% (w/v);

c. weighing 3 g of soybean lecithin, dissolving the soybean lecithin in 60 mL of phosphate buffer-PVA mixed solution; treating by using a Waring blender for 6 min (by twice, 3 min a time, at an interval of 5 min) to obtain a milk white PVA emulsion;

d. taking two 100 mL triangular flasks, respectively adding 9.00 mL of substrate solution-phosphate buffer mixed solution into the blank flask A and sample flask B, adding 15.0 mL of 95% ethanol (3.3) into the flask A, preheating in a 40±0.2° C. water bath for 5 min, then adding 1.00 mL of fermentoid solution into the flask A, adding 1 mL of an enzyme solution to be detected into the flask B, immediately mixing and starting the timer, accurately reacting in the 40±0.2° C. water bath for 15 min, immediately supplementing 15.0 mL of 95% ethanol into the flask B to terminate the reaction, and taking out;

e. respectively adding 2 drops of phenolphthalein indicator solution into the blank and sample solutions, titrating with a 0.05 mol/L sodium hydroxide standard solution until the solution becomes slightly red and remains not faded for 30 s, and recording the volume of the 0.05 mol/L sodium hydroxide standard solution consumed.

The phospholipase activity is defined as: under the conditions of certain temperature and pH, the amount of the enzyme required by hydrolyzing the substrate to generate 1 μmol of titratable fatty acids within 1 min is defined as 1 enzyme activity unit, represented by U/mL.

The phospholipase activity computing formula:

$$X_1 = \frac{(V_1 - V_2) \times c \times 50 \times n_1}{0.05} \times \frac{1}{15}$$

In the formula:

$X_1$—the enzyme activity of the sample, U/mL;

$V_1$—the volume of the sodium hydroxide standard solution consumed in the sample titrating process, the unit is (mL);

$V_2$—the volume of the sodium hydroxide standard solution consumed in the blank titrating process, the unit is (mL);

c—the concentration of the sodium hydroxide standard solution, the unit is mole per liter (mol/L);

50-1.00 mL of the 0.05 mol/L sodium hydroxide solution is equivalent to 50 μmol of fatty acids;

$n_1$—the dilution ratio of the sample;

0.05—the conversion coefficient of concentration of the sodium hydroxide standard solution;

15—the reaction time 15 min, measured in 1 min.

The experimental result shows that under 40° C. fermentation conditions, the activity of phospholipase A2 in the shake-flask fermentation supernate of the strain constructed by the embodiment is 105 U/mL, which is as 3 times as that (35 U/mL) reported in the reference [Liu A, Yu X W, Sha C, Xu Y. *Streptomyces violaceoruber* Phospholipase A2: Expression in *Pichia pastoris*, Properties, and Application in Oil Degumming. *Applied Biochemistry Biotechnology.* 2015, 175:3195-206.]. Under the 28° C., 30° C., 35° C. and 38° C. shake-flask fermentation culture conditions, the activities of phospholipase A2 in the fermentation supernate of the strain constructed in the embodiment are respectively 156 U/mL, 140 U/mL, 123 U/mL, 112 U/mL and 110 U/mL.

In the meanwhile, the expression strain from the reference [Liu A, Yu X W, Sha C, Xu Y. *Streptomyces violaceoruber* Phospholipase A2: Expression in *Pichia pastoris*, Properties, and Application in Oil Degumming. *Applied Biochemistry Biotechnology.* 2015, 175:3195-206.] is inoculated and cultured under 40° C. shake-flask culture conditions in the embodiment, the result shows that no activity of phospholipase A2 can be detected in the fermentation supernate since the original strain is not capable of resisting high temperature.

The researches above indicate that the knockout strain is capable of efficiently expressing phospholipase at the induction temperature of 40° C. or below.

Embodiment 12: Expression of Other Exogenous Genes by Knockout Strain

In order to further verify that the knockout strain is capable of highly secreting other types of exogenous proteins at high temperature, the expression in the experiment is performed by using the knockout strain as the host and using a *Rhizopus oryzae* lipase gene from the reference [Xiao-Wei Yu, Chong Sha, Yong-Liang Guo, Rong Xiao, Yan Xu*, High-level expression and characterization of a chimeric lipase from *Rhizopus oryzae* for biodiesel production, *Biotechnology for Biofuels* 2013, 6:29] and a proline protease gene sequence [Chao Kang, Xiao-Wei Yu, Yan Xu. Gene cloning and enzymatic characterization of an endoprotease Endo-Pro-*Aspergillus niger*, *Journal of Industrial Microbiology and Biotechnology,* 2013, 40: 855-864] as the targets. After an expression plasmid pPIC9K-proAROL containing the *Rhizopus oryzae* lipase gene and an expression plasmid pPIC9K-EPR containing the proline protease gene sequence are subjected to enzymatic linearization, electroporation is performed on the knockout strain. Refer to Embodiment 11 for the steps of screening of the positive strain.

The shake-flask fermentation experiment indicates that compared with the references above (by the same enzyme activity measuring method), the enzyme activities of the *Rhizopus oryzae* lipase and proline protease are respectively enhanced by 9.1 times and 2.5 times.

What is claimed is:

1. A heat-resistant recombinant *Pichia pastoris* strain CCTCC NO: M 2016278 in which a lipase gene is knocked out.

2. The recombinant *Pichia pastoris* of claim 1, wherein the lipase gene is knocked out by homologous double-crossover recombination.

3. The recombinant *Pichia pastoris* of claim 1, wherein the the *Pichia pastoris* strain CCTCC NO: M 2016278 survives incubation at 50° C. for 45 minutes.

4. A process for production of exogenous proteins, which comprises:
   providing a *Pichia pastoris* strain CCTCC NO: M 2016278 in which a lipase gene is knocked-out;
   transfecting the *P. pastoris* strain with a multi-copy integrating vector encoding an exogenous protein;
   incubating the transfected *P. pastoris* strain in growth phase culture medium under conditions suitable for growth;
   inducing expression of the exogenous protein at 40° C. or below.

5. The process of claim 4, wherein the vector is methanol-inducible, and wherein exogenous protein expression is induced by addition of methanol to the growth phase culture medium.

6. The process of claim 4, wherein the expressed exogeneous protein is secreted from the strain due to a secretion signal encoded by the vector and attached to the exogeneous protein.

7. The process of claim 4, wherein expression of the exogenous protein is induced at between 28° C. and 40° C.

8. The process of claim 4, wherein the exogenous protein is a phospholipase, a *Rhizopus oryzae* lipase, or a proline protease.

\* \* \* \* \*